(12) United States Patent
Bryning et al.

(10) Patent No.: US 7,572,409 B2
(45) Date of Patent: Aug. 11, 2009

(54) IONIC LIQUID APPARATUS AND METHOD FOR BIOLOGICAL SAMPLES

(75) Inventors: Zbigniew T. Bryning, Campbell, CA (US); Timothy Z. Liu, Fremont, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 368 days.

(21) Appl. No.: 10/444,848

(22) Filed: May 23, 2003

(65) Prior Publication Data

US 2004/0234966 A1  Nov. 25, 2004

(51) Int. Cl.
*G01N 15/06* (2006.01)
*C12Q 1/68* (2006.01)
*C12M 1/00* (2006.01)
*C12P 19/34* (2006.01)
*C07H 21/04* (2006.01)

(52) U.S. Cl. .................. 422/68.1; 422/82; 435/6; 435/91.1; 435/283.1; 435/288.6; 536/23.1

(58) Field of Classification Search ............ None
See application file for complete search history.

(56) References Cited

U.S. PATENT DOCUMENTS

| | | | |
|---|---|---|---|
| 4,121,466 A | | 10/1978 | Reichler et al. |
| 5,212,992 A | | 5/1993 | Calhoun et al. |
| 5,779,868 A | * | 7/1998 | Parce et al. ........ 204/604 |
| 6,143,496 A | * | 11/2000 | Brown et al. .......... 435/6 |
| 6,267,858 B1 | | 7/2001 | Parce et al. |
| 6,524,456 B1 | | 2/2003 | Ramsey et al. |
| 2002/0015883 A1 | | 2/2002 | Hilarius et al. |
| 2003/0075445 A1 | | 4/2003 | Woudenberg et al. |

OTHER PUBLICATIONS

Armstrong, D.W. et al., "Ionic Liquids as Matrixes for Matrix-Assisted Laser Desorption/Ionization Mass Spectrometry", *Analytical Chemistry*, 73(15):3679-3686 (2001).
Barbier, V. and Viovy, J., "Advanced Polymers for DNA Separation", *Current Opinion in Biotechnology*, 14:51-57 (2003).
Curcio, M. and Roeraade, J., "Continuous Segmented-Flow Polymerase Chain Reaction for High-Throughput Miniaturized DNA Amplification", *Analytical Chemistry*, 75(1):1-7 (2003).
Leone, A.M. et al., "An Ionic Liquid Form of DNA: Redox-Active Molten Salts of Nucleic Acids", *J. Am. Chem. Soc.*, 123(2): 218-222 (2001).
Yanes, E.G. et al., "Capillary Electrophoretic Application of 1-Alkyl-3-methylimidazolium-Based Ionic Liquids", *Analytical Chemistry*, 73(16):3838-3844 (2001).
Rogers, R.D. et al, "Room Temperature Ionic Liquids as Alternatives to Organic Solvents in Liquid/Liquid Extraction", http://bama.ua.edu/~rdrogers/webdocs/RTIL/s1d001.htm, 1-34.

(Continued)

*Primary Examiner*—B J Forman (57) ABSTRACT

Apparatus and method for handling biological samples. Segments of ionic liquid can provide voltage across segments of immiscible liquid to concentrate or separate charged species in the biological samples. Reactants in biological samples can be contacted and reacted in segments of immiscible liquid.

31 Claims, 5 Drawing Sheets

OTHER PUBLICATIONS

Qin et al., "1,3-Dialkylimidazolium-Based Room-Temperature Ionic Liquids As Background Electrolyte and Coating Material In Aqueous Capillary Electrophoresis," Journal of Chromatography, vol. 985, No. 1-2, Jan. 24, 2003, pp. 447-454.

Vaher et. al., "Ionic Liquids As Electrolytes for Nonaqueous Capillary Electrophoresis," Electrophoresis, vol. 23, 2002, pp. 426-430.

Seddon, "Ionic Liquids For Clean Technology," Journal of Chemical Technology and Biotechnology, vol. 68, No. 4, Apr. 1, 1997, pp. 351-356.

International Search Report from PCT/US04/016591, Mailed Oct. 19, 2004.

* cited by examiner

IONIC LIQUID APPARATUS AND METHOD FOR BIOLOGICAL SAMPLES

FIELD

The present teachings relate to ionic liquid handling of biological samples.

INTRODUCTION

In the biological field, reactions of biological samples can include polymerase chain reaction (PCR) and other reactions such as ligase chain reaction, antibody binding reaction, oligonucleotide ligations assay, and hybridization assay. These and other biological reactions, as well as separations and concentrations can include handling the biological samples while in an aqueous solution. The term "biological samples" as used herein can refer to components in biological fluids (e.g. blood, lymph, urine, sweat, etc.), reactants, and/or reaction products, any of which can include peptides, nucleotides, or other biological charged species. Electrophoresis is known in the art of handling biological samples as a process of handling, including concentrating and/or separating charged species in the biological samples. Capillary electrophoresis can utilize small volumes of liquid that tend to evaporate and bubble at the electrodes. Electrochemical reactions can occur at the interface of an electrode and an aqueous solution. The electrochemical reactions can include electrolysis of water to form hydrogen gas and oxygen gas, i.e., generating bubbles at the electrode. It can be desirable to provide a bubbleless electrode for electrophoresis within aqueous solutions, including capillary electrophoresis. Ionic liquids can provide an intermediate medium that can substantially reduce electrochemical reactions at the interface of the electrode and the ionic liquid. Instead of electron transfer at the electrode that can result in electrolysis and bubbles around the electrode, ions can be transferred at the interface of the ionic liquid and the aqueous solution to provide electrophoresis of charged biological samples in the aqueous solution. Similar advantages can be realized for biological samples in non-aqueous solutions.

SUMMARY

According to various embodiments, an apparatus for handling biological samples can include a channel, and a plurality of liquid segments in the channel, wherein the plurality of segments includes an immiscible liquid segment between ionic liquid segments. According to various embodiments, an apparatus for handling biological samples can include a plurality of segments including an immiscible liquid segment between ionic liquid segments, wherein voltage is applied across the immiscible liquid segment to provide electrophoresis. According to various embodiments, an apparatus for handling biological samples can include a plurality of segments including an ionic liquid segment between immiscible liquid segments, wherein a voltage is applied across the ionic liquid segment, wherein the voltage is adapted to break the ionic liquid segment and contact the immiscible liquid segments.

According to various embodiments, a method for handling biological material can include providing a plurality of segments including an immiscible liquid segment between ionic liquid segments, and providing a voltage across the immiscible liquid segment. According to various embodiments, a method for handling biological samples can include providing an ionic liquid segment between a first immiscible liquid segment and a second immiscible liquid segment, wherein the first immiscible liquid segment includes a first reactant and the second immiscible liquid segment includes a second reactant, providing a voltage across the ionic liquid segment, breaking the ionic liquid segment, and contacting the first reactant and the second reactant. According to various embodiments, a method for handling biological samples can include providing an immiscible liquid segment between two ionic liquid segments, and providing a voltage across the immiscible liquid segment. According to various embodiments, a method for forming a plurality of segments of biological samples can include providing a channel including an inlet, positioning the inlet in a container including an immiscible material layer and an ionic liquid layer, wherein the layers are immiscible, coating the channel with the ionic liquid, aspirating an immiscible liquid segment into the inlet.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings.

DESCRIPTION OF VARIOUS EMBODIMENTS

Reference will now be made to various exemplary embodiments, examples of which are illustrated in the accompanying drawings. Wherever possible, the same reference numbers are used in the drawings and the description to refer to the same or like parts.

The term "ionic liquids" refers to salts that are liquid over a wide temperature range, including room temperature. Ionic liquids have been described at http://bama.ua.edu/~rdrogers/webdocs/RTIL. Variations in cations and anions can produce millions of ionic liquids, including chiral, fluorinated, and antibacterial ionic liquids. The large number of possibilities can provide ionic liquid properties specific to applications. Ionic liquids can be desirable because they are environmentally-friendly alternatives to organic solvents for liquid/liquid extractions, catalysis, separations, and electrochemistry. Ionic liquids can reduce the cost, disposal requirements, and hazards associated with volatile organic compounds. Exemplary properties of ionic liquids are high ionic conductivity, non-volatility, non-flammability, high thermal stability, wide temperature for liquid phase, highly solvability, and non-coordinating. The choice of cation and anion determine the physical properties (e.g. melting point, viscosity, density, water solubility, etc.). Cations can be big, bulky, and asymmetric contributing to the low melting points, and anions contributing more to the overall characteristics such as air and water stability. Melting point for ionic liquids can be changed by structural variation of one of the ions or combining different ions. Examples of ionic liquid cations include N-butylpyridinium and 1-alkyl-3-methylimidazolium(1,3-diaalkylimidazolium; alkyl mim). Examples of anions include $[PF_6]^-$ that is immiscible in water and $[BF_4]^-$ that is miscible in water depending on the ratio of ionic liquid to water, system temperature, and alkyl chain length of cation. Other anions include triflate (TfO; $CF_3SO_2^-$), nonaflate (NfO; $CF_3(CF_2)_3SO_2^-$), bis(triflyl)amide (Tf$_2$N; $(CF_3SO_2)_2N^-$), trifluoroacetate (TA; $CF_3CO_2^-$), and heptaflurorobutanoate (HB; $CF_3(CF_2)_3SO_2^-$). One type of ionic liquids includes haloaluminates such as chroloaluminate. Chloro and bromo ionic liquids can have large electrochemical windows because molten salts prevent solvation and solvolysis of the metal ion species. Further examples include 1-alkyl-3-methylimidazoliuim [$PF_6$] such as 1-decyl-3-methylimidazolium [$PF_6$], 1-butyl-3-methylimidazolium [$PF_6$], and 1-ethyl-3-methylimidzolium with [$NO_3$], [$NO_2$], [$MeCO_2$], [$SO_4$], [$PF_6$], [TfO], [NfO], [$BF_4$], [Tf$_2$N], and [TA], N-alkylpyridinium chloride or N-alkylpyridium nickel chloride with $C_{12}$ to $C_{18}$ alkyl chains, and any variations of these as is known to one skilled in the art of ionic fluids. Sources of ionic liquids include Aldrich (Milwaukee, Wis.), Elementis Corp. (Durham, UK), SACHEM (Austin, Tex.), TCI (Tokyo, Kasei), and QUILL (N. Ireland). Other examples include 1-ethyl-3-methylimidazolium bis[1,2-benzenediolato-O,O'] borate, 1-ethyl-3-methylimidazolium bis[salicylato]borate, 1-ethyl-3-methylimidazolium bis[oxalato]borate, and other compounds described in U.S. Pub. No. 2002/0015883 to Hilarius, et al., and N-alkyl-N'-alkoxyalkylimidazolium ionic liquids described in Japanese Publication 2002/003478.

According to various embodiments, FIGS. 1-7 illustrate portions of an apparatus for concentration, separation, reaction, or otherwise handling a biological sample. According to various embodiments, FIG. 1A illustrates reservoirs 10 containing ionic liquid 12, electrode 14, and capillary 16. Capillary 16 can be shaped such that its ends are submerged below the surface of the ionic liquid 12 in the reservoir 10. Submerging the openings of capillary 16 provides a continuous ionic liquid segment from the reservoir 10 and into the capillary 16 on either end of a segment of immiscible liquid 18. Electrode 14 can be a platinum wire or any other appropriate material to apply a current across the ionic liquid segments and immiscible liquid segment. According to various embodiments, a u-shaped capillary can be constructed from a 10 microliter glass micropipette that has an internal diameter of 0.5 millimeters and a length of 50 millimeters. This material and dimensions are illustrative and can be altered by one skilled in the art of microfluidics to any material and dimensions.

Figure 1A:
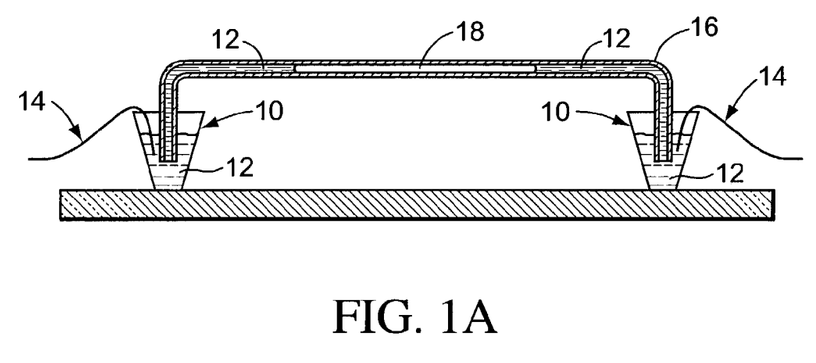
FIG. 1A illustrates a cross-section of various embodiments of a capillary with an immiscible liquid segment between two ionic liquid segments.

According to various embodiments, the apparatus can provide handling of biological samples, including concentration, separation, and/or reaction of components, reactants, and/or reaction products in the immiscible liquid at either end of the segment of immiscible liquid by applying a voltage at the electrodes as is known in the art of electrophoresis.

The terms "immiscible liquid" herein refer to liquids that do not mix with ionic liquids. Immiscible liquids can be aqueous (containing water), or they can be non-polar organic solvents such as DMF, DMSO, xylene, octane, perfluorodecalin, and other hydrocarbons that can be at least partially soluble with the biological material. Immiscible liquids can be aqueous or organic because ionic liquids can be hydrophilic or hydrophobic. According to various embodiments, hydrophobic ionic liquid segments of 1-butyl-3-methylimidazolium hexafluorophosphate (BMI $PF_6$) and 1,2-dimethyl-3-butylimidazolium hexafluorophosphate (DMBI $PF_6$) from SACHEM, Inc. (Austin, Tex.) can be used with aqueous immiscible liquid segments, and hydrophilic ionic liquid segments of 1-ethyl-3-methylimidazolium tetrafluoroborate (EMI $BF_4$) and 1-ethyl-3-methylimidazolium trifluoromethanesulfonate (EMI TFMS) from TCI (Tokyo Kasei) can be used with non-polar organic solvent immiscible liquid segments. The ionic liquids can be purified by repeated dissolving in acetone and washing with water and xylene, phase separation, and drying in vacuum.

Figure 1B:
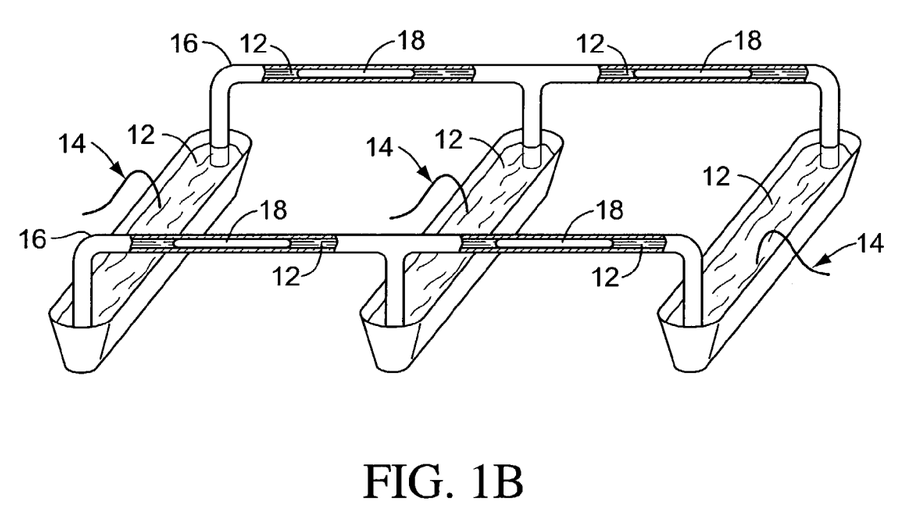
FIG. 1B illustrates a view of various embodiments of a parallel capillaries with a plurality of immiscible liquid segments with common ionic liquid segments.
Figure 1C:
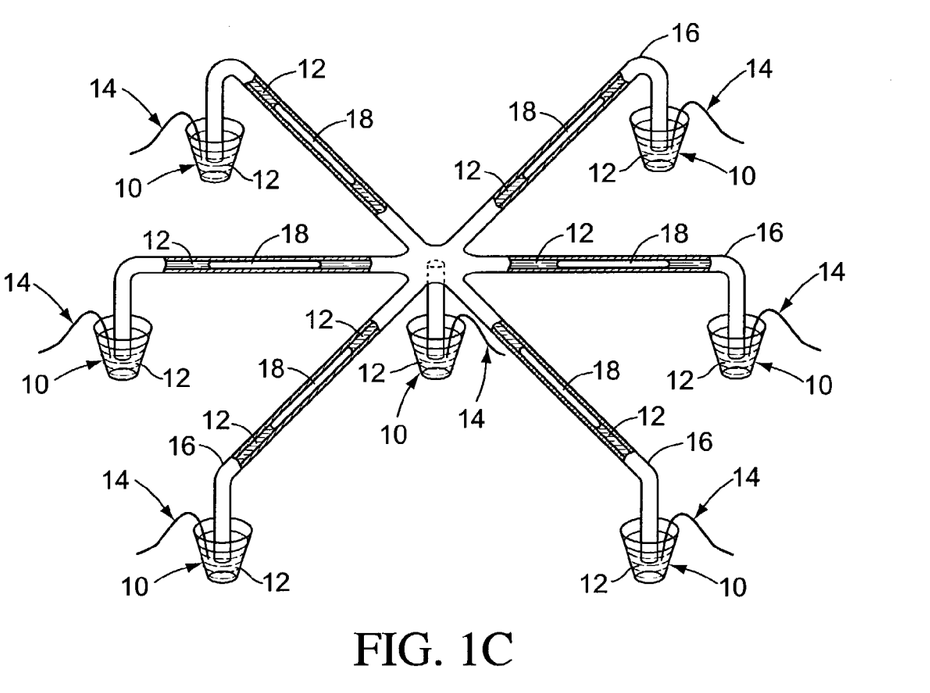
FIG. 1C illustrates a view of various embodiments of a branched capillary with a plurality of immiscible liquid segments with wheel and spoke ionic liquid segments.

According to various embodiments, FIGS. 1B and 1C illustrate different embodiments of capillaries. FIG. 1B illustrates an embodiment where several reservoirs 10 comprise ionic liquid 12, electrode 14, and parallel capillaries 16. Segments of immiscible liquid 18 can be in parallel alternated between segments of ionic liquid 12. According to various embodiments, as illustrated in FIG. 1C, reservoirs 10 can be arranged in a wheel and spoke configuration. The capillary 16 has radial branches for each reservoir 10, each branch containing a segment of immiscible liquid 18 between segments of ionic liquid 12. Each branch of immiscible liquid segment can be concentrated and/or contacted with any other immiscible liquid segment thereby controlling the concentration and contact of the immiscible liquid segments both separately and in sequence.

Figure 1D:
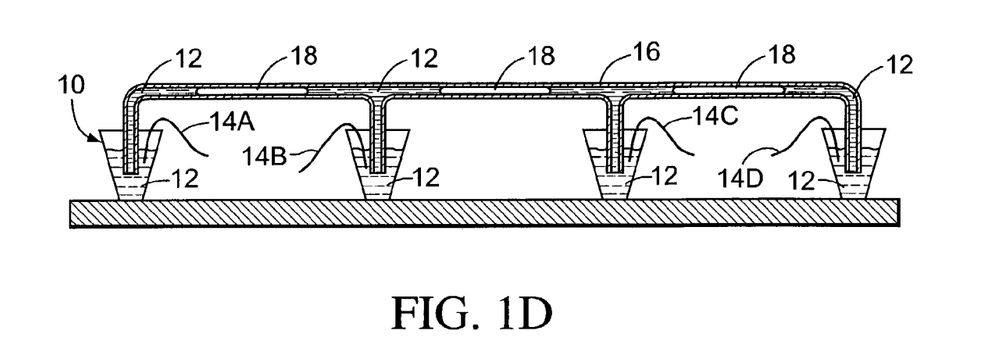
FIG. 1D illustrates a cross-section of various embodiments of a capillary with a plurality of immiscible liquid segments arranges in series.

According to various embodiments, as illustrated in FIG. 1D, handling can be provided by segments in series. A first concentration can be achieved by providing a voltage across the first segment of immiscible liquid 18 by making electrode 14A negative and electrode 14B positive. The negatively charged species in the first segment of immiscible liquid 18 can be concentrated toward the end of the segment immiscible liquid 18 that is closest to electrode 14B. A second concentration can be achieved by providing a voltage across the second segment of immiscible liquid 18 by making electrode 14C negative. The negatively charged species in the second segment of immiscible liquid 18 can be concentrated toward the end of the segment of immiscible liquid that is closest to electrode 14B. As described below, sufficient voltage can be applied across electrodes 14A, 14B, and 14C to break the segment of ionic liquid 12 between the segments of immiscible liquid 18 and to contact the concentrated charged species in the first and second segments of immiscible liquid 18. The process can be repeated to contact the concentrated charged species in the third segment of immiscible liquid 18 with the reaction product of the first and second segments of immiscible liquid 18. At any point, the charged species of the biological sample, including reactants and reaction products can be concentrated by applying voltage across any combination of electrodes 14A, 14B, 14C and 14D. The biological samples can be concentrated and detected by scanning the capillary where the charged species have been concentrated. Detection can include absorbance, spectroscopy (fluorescence or Raman), reflectance, colorimetry and any other detection known in the art of analysis of biological materials.

FIGS. 1A-1D are illustrative and any configuration that provides concentration, contacting, and otherwise handling of a biological material can be used.

Figure 2A:
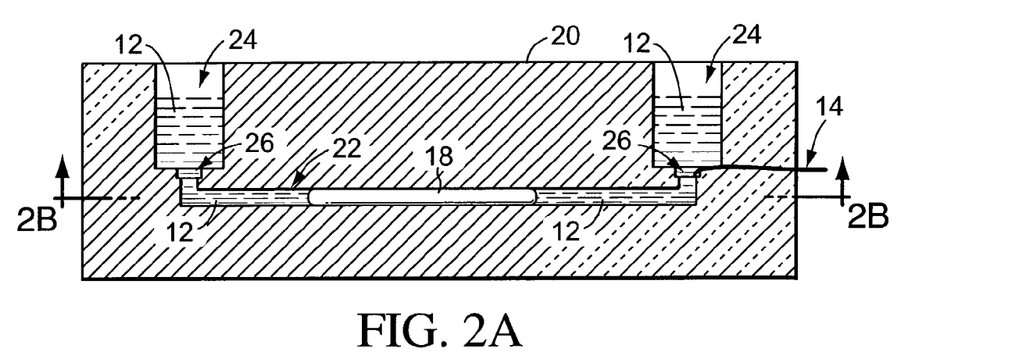
FIG. 2A-2B illustrate cross-sections of various embodiments of a channel with an immiscible liquid segment between two ionic liquid segments.
Figure 2B:
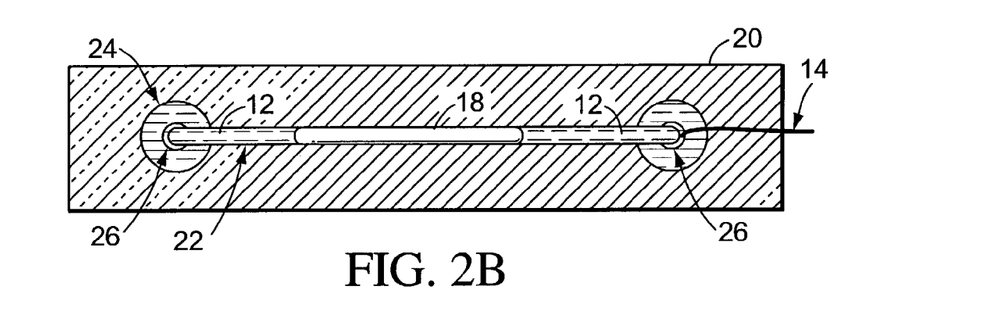
Figure 2C:
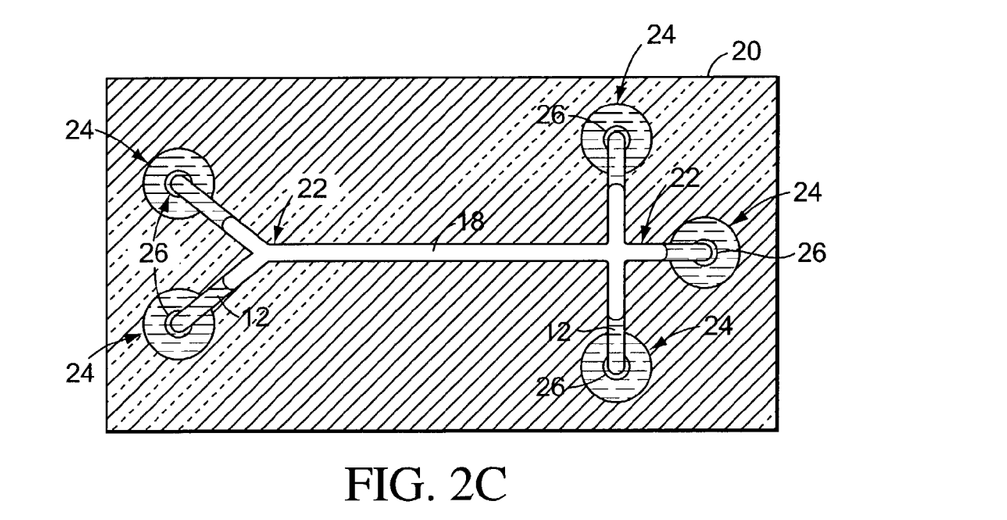
FIG. 2C illustrates a cross-section of various embodiments of a branched channel with an immiscible liquid segment between five ionic liquid segments.

According to various embodiments, channels, including microchannels can be used instead of capillaries. Microchannels can be desirable channels because they provide several advantages over capillaries. Microchannels can facilitate manufacturing and manipulation of liquids for filling access holes to prevent evaporation. FIGS. 2A-2C illustrate various embodiments where segments of ionic liquid 12 and segments of immiscible fluid 18 can be contained in channels 22. FIG. 2A is a side view and FIG. 2B is cut-away view along plane 2B as indicated in FIG. 2A. Access holes 24 form nodes 26 with channel 22. Access holes 24 are filled with ionic fluid 12 on either side of the segment of immiscible liquid 18. The channel 22 can be positioned inside substrate 20. The substrate can be made of glass or plastic. The ionic liquid segment and immiscible liquid segment were introduced by applying vacuum and/or pressure. According to various embodiments, channel 22 can be a microchannel with dimensions of 100 microns width and 110 millimeters length with a 50 micron dip. This material and dimensions are illustrative and can be altered by one skilled in the art of microfluidics to any material and dimensions. FIG. 2A illustrates electrode 14 at one node 26. The other electrode (not shown) at the other node 26 can be embedded into substrate 20 and activated externally without reaching through substrate 20 to node 26. Therefore, ionic liquid can be refilled through access holes without interfering with the embedded electrode.

According to various embodiments, as illustrated in FIG. 2B, channel 22 can be branched with multiple access holes 24 and nodes 26. The segment of immiscible liquid 18 can be branched with each branch ending in a segment of ionic liquid 12. By applying voltage to different nodes 26 via their respective electrodes (not shown) the biological sample can be handled in any branch of the channel 22 such that concentrations of charged species in the biological sample can be provided in any branch.

According to various embodiments, platinum wire electrodes immersed in ionic liquid segments can be robust with no degradation. Channels loaded with immiscible liquid segments in between ionic liquid segments can be stable for long periods of time and can be stored and used for days. The electric connection between the electrode and the ionic liquid can be stable with no change in current over time and substantially no bubbles at the electrode-ionic liquid interface and substantially no bubbles between the ionic liquid and immiscible liquid interface.

Figure 3A:
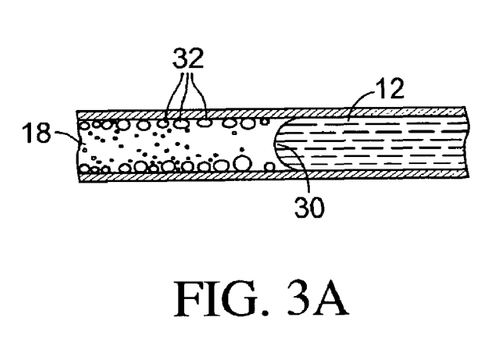
FIG. 3A illustrates a cross-section of various embodiments of a channel containing ionic liquid loaded with immiscible liquid.
Figure 3B:
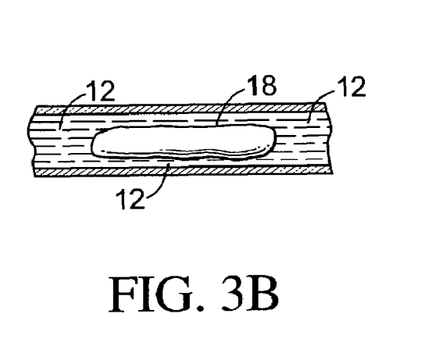
FIG. 3B illustrates a cross-section of various embodiments of a channel containing ionic liquid loaded with immiscible liquid where the channel has been surface treated.

According to various embodiments, the interior surface of channels, including microchannels and capillaries, can be made of clean glass. Clean glass can be coated by the immiscible liquid if the immiscible liquid is aqueous. Such coating can allow the aqueous immiscible liquid segments to creep around the ionic liquid segments. Such creeping can allow the aqueous immiscible liquid segment to reach the electrode and evaporate, especially at elevated temperatures, for example 95° C. This can be substantially prevented by silanizing the interior surface of the channel as is known in the art of hydrophobic surface treatment. In silanized channels, the ionic liquid coats the interior surface. FIGS. 3A and 3B illustrate the effect of silanization. FIG. 3A illustrates a channel without silanization where the segment of immiscible liquid 18 can coat the interior surface of the channel leaving droplets 32 of ionic liquid 12. The segment of ionic liquid 12 can form a meniscus 30 with the segment of immiscible liquid 18 curved toward the immiscible liquid because the ionic liquid 12 coats the interior surface of the channel. FIG. 3B illustrates a channel with silanization where the ionic liquid 12 can coat the interior surface of the channel enveloping immiscible liquid 18 coaxially in segments of immiscible liquid 18. The term "segment" refers to plug of liquid whether or not another liquid coats the channel. According to various embodiments, FIG. 3B illustrates a segment of immiscible liquid 18 between two segments of ionic liquid 12. The channel at the position of the segment of immiscible liquid 18 can be coated with ionic liquid 12, so that the segment of immiscible liquid 18 includes a coating of ionic liquid on the interior surface of the channel.

Figure 4A:
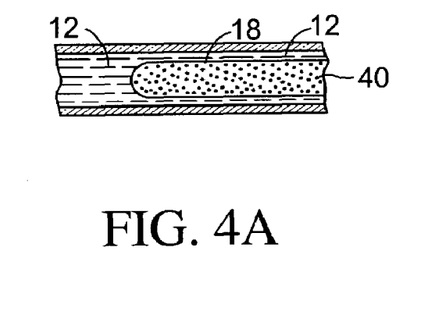
FIG. 4A illustrates a cross-section of various embodiments of a channel containing ionic liquid and immiscible liquid with biological material.
Figure 4B:
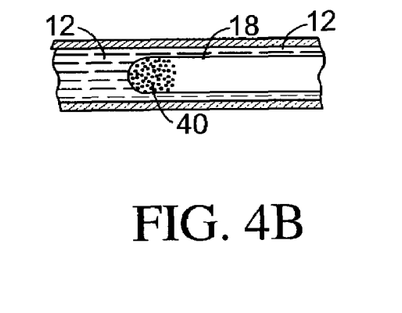
FIG. 4B illustrates a cross-section of various embodiments of a channel containing ionic liquid loaded with immiscible liquid where the biological material has been concentrated toward the immiscible liquid.

According to various embodiments, FIGS. 4A and 4B illustrate the concentration of biological material in the immiscible liquid segment. FIG. 4A illustrates a segment of immiscible liquid 18 with biological material 40 distributed throughout the immiscible liquid 18. According to various embodiments, charged species 40 can be oligonucleotides, DNA, RNA, proteins, or other charged species of interest in the biological sample. FIG. 4B illustrates applying a voltage drop between the segments of ionic liquid 12 bounding, either directly or indirectly, the segment of immiscible liquid 18. Applying the voltage across the segment of immiscible liquid 18 can result in a concentration of charged species 40 in the segment of immiscible liquid 18 at the interface with ionic liquid 12 closest to the electrode (not shown) of opposite charge to the charge of charged species 40. This configuration is illustrative and can be altered by one skilled in the art of electrophoresis to a voltage appropriate for a particular ionic liquid for a charged species of interest. The term "concentration" and grammatical variations thereof as used herein refers to the process of forcing charged species against diffusion from an area of low concentration to an area of high concentration as known in the art of electrophoresis.

Figure 5A:
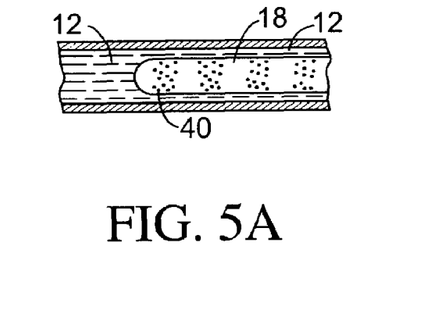
FIG. 5A illustrates a cross-section of various embodiments of a channel containing ionic liquid loaded with immiscible liquid wherein the charged species in the biological sample separates into distinct bands.
Figure 5B:
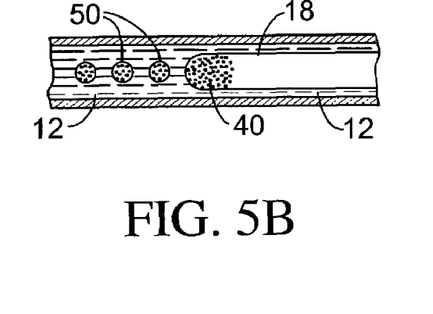
FIG. 5B illustrates a cross-section of various embodiments of a channel containing ionic liquid loaded with immiscible liquid wherein the immiscible liquid forms droplet in the ionic liquid.

According to various embodiments, a concentration can be combined with a separation. The term "separation" and grammatical variations thereof as used herein refers to the process of separating charged species based on size within immiscible liquid segments. Separation can result from differentiating the charged species by charge/size ratio by using a separation polymer as known in the art of electrophoresis. The term "polymer" as used herein refers to oligomers, homopolymers, and copolymers and mixtures thereof as known in the art of polymer chemistry. According to various embodiments, as illustrated in FIG. 5A, charged species 40 can be separated into different bands based on charge/size ratio. According to various embodiments, as illustrated in FIG. 5B, charged species 40 that are separated can be segregated at the interface of the segment of immiscible liquid 18 and the segment of ionic liquid 12 by being enveloped in droplets 50 of immiscible liquid 18. Each droplet 50 can capture charged species 40 of different size as they become concentrated at the interface. The timing of droplet 50 formation and charged species 40 travel can be correlated according to the properties of the immiscible liquid 18 as is known in the art of electrophoresis.

Figure 6A:
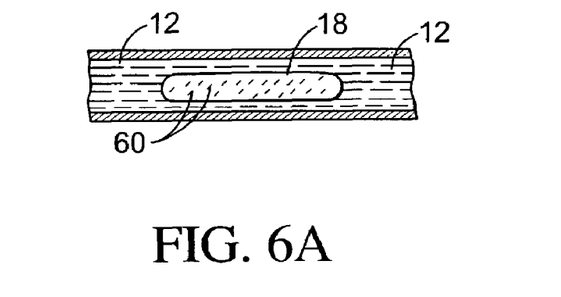
FIG. 6A illustrates a cross-section of various embodiments of a channel containing ionic liquid loaded with immiscible liquid where the immiscible liquid contains reactants.
Figure 6B:
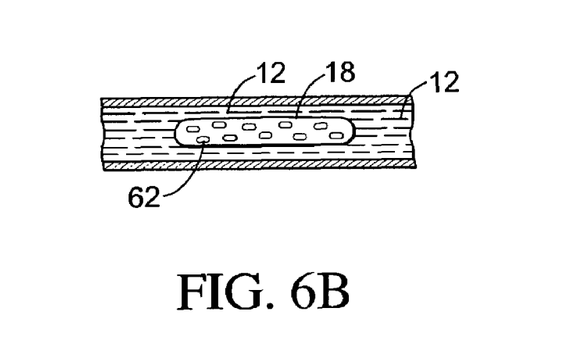
FIG. 6B-C illustrate a cross-section of various embodiments of a channel containing ionic liquid loaded with immiscible liquid where the immiscible liquid contains reaction products.
Figure 6C:
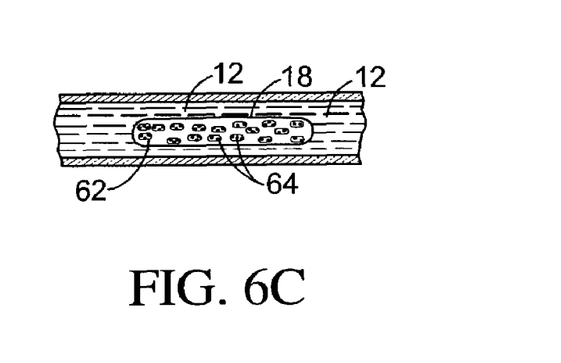

According to various embodiments, a reaction can be performed within the segment of immiscible liquid. The term "reaction" refers to the process of reacting reactants to form reaction products within the immiscible liquid segments. Reaction can result from providing reaction conditions such as temperature changes to the reactants within the segment of immiscible liquid. Several biological reactions are described herein. As illustrated in FIG. 6A, the segment of immiscible liquid 18 can include reactants 60 and can be positioned between two segments of ionic liquid 12. Reactants 60 can react under the proper reaction conditions to produce reaction products 62, as illustrated in FIG. 6B. Reaction products 62 can include charged species 64, as illustrated in FIG. 6C. According to various embodiments, charged species 64 can be concentrated as illustrated in FIG. 4B. Concentration can provide better detection of the reaction products 62 by absorbance, spectroscopy (fluorescence or Raman), reflectance, colorimetry and any other detection known in the art of analysis of biological materials.

Figure 7A:
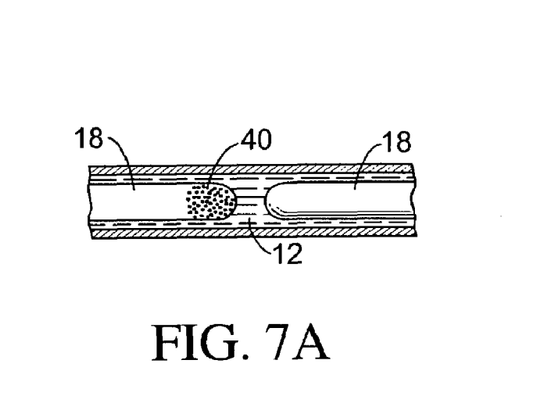
FIG. 7A illustrates a cross-section of various embodiments of a channel containing ionic liquid loaded with immiscible liquid where the biological material is concentrated toward the ionic liquid.
Figure 7B:
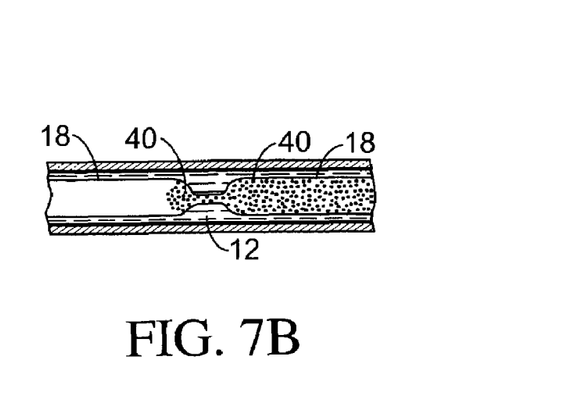
FIG. 7B illustrates a cross-section of various embodiments of a channel containing ionic liquid loaded with immiscible liquid with biological material where the immiscible liquid breaks through the ionic liquid.

According to various embodiments, the segment of ionic liquid can act as a "valve" and break to allow different segments of immiscible liquid to mix. As illustrated in FIG. 7A, the charge species 40 can be concentrated in a first segment of immiscible liquid 18 as described above and illustrated in FIG. 4B. A second segment of immiscible liquid 18, separate from the first segment of immiscible liquid 18, can be positioned adjacent to first segment of immiscible liquid 18 and separated by a segment of ionic liquid 12. Voltage applied across the first and second segments of immiscible liquid 18 can be increased to provide sufficient current to break the segment of ionic liquid 12, as illustrated in FIG. 7B. Charged species 40 can move through the opening of immiscible liquid 18 between the segments of immiscible liquid 18 provided by the break toward the electrode of opposite charge to the charge of charged species 40.

According to various embodiments, the ionic liquid segments and immiscible liquid segments can be static as the embodiments illustrated in FIGS. 1-7 or they can be in a continuous segmented flow. According to various embodiments, continuous segmented flow can provide the ability to pass the segments flowing through a channel through different process conditions such as water baths or other heating/cooling devices to thermally cycle the segments as in PCR, for example.

According to various embodiments, a method for handling biological material can include providing a plurality of segments can include an immiscible liquid segment between ionic liquid segments, and providing a voltage across the immiscible liquid segment. The immiscible liquid segment can include a biological sample. The biological sample can be adapted for at least one of PCR, ligase chain reaction, antibody binding reaction, oligonucleotide ligations assay, and hybridization assay. The immiscible liquid segment can include at least one of aqueous and non-polar organic solvents.

According to various embodiments, a method for handling biological samples, can include providing an ionic liquid segment between a first immiscible liquid segment and a second immiscible liquid segment, wherein the first immiscible liquid segment can include a first reactant and the second immiscible liquid segment can include a second reactant, providing a voltage across the ionic liquid segment, breaking the ionic liquid segment, and contacting the first reactant and the second reactant. The first reactant and the second reactant can be adapted for at least one of PCR, ligase chain reaction, antibody binding reaction, oligonucleotide ligations assay, and hybridization assay. The immiscible liquid segment can include at least one of aqueous and non-polar organic solvents. The method can include detecting reaction products by at least one of absorbance, fluorescence spectroscopy, Raman spectroscopy, reflectance, and colorimetry.

According to various embodiments, a method for handling biological samples can include providing an immiscible liquid segment between two ionic liquid segments, and providing a voltage across the immiscible liquid segment. The method can include concentrating a charged species in the immiscible liquid. The method can include detecting the concentrated charged species. The method can include separating a charged species in the immiscible liquid. The method can include detecting the separated charged species.

According to various embodiments, a method for forming a plurality of segments of biological samples can include providing a channel can include an inlet, positioning the inlet in a container including an immiscible material layer and an ionic liquid layer, wherein the layers are immiscible, coating the channel with the ionic liquid, aspirating an immiscible liquid segment into the inlet. The coating can include positioning the inlet in the ionic liquid layer and suctioning ionic liquid. The aspirating can include positioning the inlet from the ionic liquid layer to the immiscible material layer and suctioning immiscible material.

EXAMPLES

The following examples are illustrative and are non-limiting to the present teachings.

Example 1

Concentration of Charged Species

Example 1 illustrates the concentration of charged species in a biological sample. Oligonucleotides were dissolved in water and 310 buffer to form a segment of immiscible fluid between two segments of BMI $PF_6$ ionic liquid. The negatively charged oligonucleotides moved quickly toward the positive electrode. Within a period of 2-5 minutes after applying up to 500 volts (1.5 microamps for each 100 volts) the negatively charged oligonucleotides concentrated in the segment of immiscible liquid at the ionic liquid interface closest to the positive electrode. Example 1 can be illustrated by FIG. 4B.

Example 2

Separation of Charged Species

Example 2 illustrates the separation of charged species. Precision Plus Protein Standard All Blue from Bio-Rad (Hercules, Calif.), which contains ten different protein groups from 10 kilodaltons to 250 kilodaltons stained with Coomassie dye, can be dissolved in buffer, which contains glycerol, SDS, Tris, DTT, EDTA, and $NaN_3$ to form a segment of immiscible liquid between two segments of EMI TFMS ionic liquid. Within a period of 2-5 minutes after applying up to 500 volts, ten protein bands can be separated in the immiscible liquid. Example 2 can be illustrated by FIG. 5A.

Example 3

Separation of Charged Species

Example 3 illustrates the separation of charged species in a biological sample. Precision Plus Protein Standard All Blue from Bio-Rad (Hercules, Calif.), which contains ten different protein groups from 10 kilodaltons to 250 kilodaltons stained with Coomassie dye, can be dissolved in separation polymer, such as POP-6™ (Applied Biosystems) to form a segment of immiscible liquid between two segments of EMI TFMS ionic liquid. Within a period of 2-5 minutes after applying up to 1000 volts, ten protein bands can be separated in the immiscible liquid to break through the ionic liquid interface and form droplets of immiscible liquid for each band. Example 3 can be illustrated in FIG. 5B. The droplets of immiscible liquid can be moved to different positions in an ionic liquid system similar to that illustrated in FIG. 2B.

Example 4

Reaction to Form Reaction Products with Charged Species

Example 4 illustrates reaction to form reaction products with charged species in a biological sample. Stoichiometric amounts of TaqMan reagents (75 nl) were dissolved in a buffer to form a segment of immiscible liquid between two segments of $BMI\ PF_6$ ionic liquid inside a silanized microchannel chip. The ionic liquid was exposed to atmosphere. The chip was placed on a modified thermocycler and cycled 20 times from 60° C. to 95° C. The thermocycling reaction amplified the DNA. Voltage was applied across the ionic liquid segments and the DNA was concentrated at the positive electrode. The fluorescence signal was measured under a fluorescence microscope. Example 4 can be illustrated by FIGS. 6A-6C and FIG. 4B.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a charged species" includes two or more different charged species. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. An apparatus for handling biological samples, comprising:
    a channel; and
    a plurality of liquid segments in said channel, wherein said plurality of segments comprises an immiscible liquid segment between ionic liquid segments, wherein the immiscible liquid segment comprises the biological sample and the ionic liquid segment comprises a liquid salt.

2. The apparatus of claim 1, wherein a voltage is applied across said immiscible liquid segment.

3. The apparatus of claim 2, wherein said immiscible liquid segment comprises a separation polymer.

4. The apparatus of claim 1, wherein said biological sample is adapted for at least one of PCR, ligase chain reaction, antibody binding reaction, oligonucleotide ligations assay, and hybridization assay.

5. The apparatus of claim 1, wherein said channel is a capillary or a microchannel.

6. The apparatus of claim 1, wherein said immiscible liquid segment comprises at least one of aqueous and non-polar organic solvents.

7. An apparatus for handling biological samples, comprising:
    a plurality of segments comprising an immiscible liquid segment between ionic liquid segments, wherein voltage is applied across said immiscible liquid segment to provide electrophoresis, and wherein the immiscible liquid segment comprises the biological sample and the ionic liquid segment comprises a liquid salt.

8. The apparatus of claim 7, wherein said voltage is applied between a first electrode in a first segment of ionic liquid and to a second electrode in a second segment of ionic liquid.

9. The apparatus of claim 7, wherein said biological sample is adapted for at least one of PCR, ligase chain reaction, antibody binding reaction, oligonucleotide ligations assay, and hybridization assay.

10. The apparatus of claim 7, wherein said immiscible liquid segment comprises a separation polymer.

11. The apparatus of claim 7, further comprising a channel, wherein said channel is a capillary or a microchannel.

12. The apparatus of claim 7, wherein said immiscible liquid segment comprises at least one of aqueous and non-polar organic solvents.

13. An apparatus for handling biological samples, comprising:
a plurality of segments comprising an ionic liquid segment between immiscible liquid segments, wherein a voltage is applied across said ionic liquid segment, wherein said voltage is adapted to break said ionic liquid segment and contact said immiscible liquid segments, and wherein the immiscible liquid segment comprises the biological sample and the ionic liquid segment comprises a liquid salt.

14. The apparatus of claim 13, wherein said immiscible liquid segments comprise reactants.

15. The apparatus of claim 14, wherein said reactants are adapted for at least one of PCR, ligase chain reaction, antibody binding reaction, oligonucleotide ligations assay, and hybridization assay.

16. The apparatus of claim 13, wherein said channel is a capillary or a microchannel.

17. The apparatus of claim 13, wherein said immiscible liquid segment comprises at least one of aqueous and non-polar organic solvents.

18. A method for handling a biological sample comprising:
providing a plurality of liquid segments in a channel, the plurality of liquid segments comprising an immiscible liquid segment between ionic liquid segments wherein the immiscible liquid segment comprises the biological sample and the ionic liquid segments comprise a liquid salt; and
providing a voltage across said immiscible liquid segment.

19. The method of claim 18, wherein said biological sample is adapted for at least one of PCR, ligase chain reaction, antibody binding reaction, oligonucleotide ligation assay, and hybridization assay.

20. The method of claim 18, wherein said immiscible liquid segment comprises at least one of aqueous and non-polar organic solvents.

21. The method of claim 18, further comprising concentrating a charged species in said immiscible liquid.

22. The method of claim 21, further comprising detecting the concentrated charged species.

23. The method of claim 18, further comprising separating a charged species in said immiscible liquid.

24. The method of claim 23, further comprising detecting the separated charged species.

25. A method for handling biological samples comprising:
providing an ionic liquid segment between a first immiscible liquid segment and a second immiscible liquid segment in a channel, wherein said first immiscible liquid segment comprises a biological sample and said second immiscible liquid segment comprises a reactant, and said ionic liquid segment comprises a liquid salt;
providing a voltage across said ionic liquid segment;
breaking said ionic liquid segment; and
contacting said biological sample and said reactant.

26. The method of claim 25, wherein said biological sample and said reactant are adapted for at least one of PCR, ligase chain reaction, antibody binding reaction, oligonucleotide ligation assay, and hybridization assay.

27. The method of claim 25, wherein said immiscible liquid segment comprises at least one of aqueous and non-polar organic solvents.

28. The method of claim 25, further comprising detecting reaction products by at least one of absorbance, fluorescence spectroscopy, Raman spectroscopy, reflectance, and colorimetry.

29. A method for forming a plurality of segments of biological samples comprising:
providing a channel comprising an inlet;
positioning said inlet in a container comprising an immiscible material layer and an ionic liquid layer, wherein said layers are immiscible;
coating said channel with said ionic liquid; and
aspirating an immiscible liquid segment into said inlet, thereby forming a plurality of liquid segments comprising an immiscible liquid segment between two segments of ionic liquid wherein the immiscible liquid segment comprises a biological sample and the ionic liquid segments comprise liquid salts.

30. The method according to claim 29, wherein said coating comprises positioning said inlet in said ionic liquid layer and suctioning ionic liquid.

31. The method according to claim 30, wherein said aspirating comprises positioning said inlet from said ionic liquid layer to said immiscible material layer and suctioning immiscible material.

* * * * *